United States Patent [19]

Kikuchi et al.

[11] Patent Number: 4,605,419
[45] Date of Patent: Aug. 12, 1986

[54] 5,8-DIHYDROXY NAPHTHALENE-1,4-DIONE DERIVATIVE AND A HAIR DYE COMPOSITION CONTAINING THE SAME

[75] Inventors: Masashi Kikuchi; Masahiro Matsuoka, both of Yokohama, Japan

[73] Assignee: Shiseido Company Ltd., Tokyo, Japan

[21] Appl. No.: 725,069

[22] Filed: Apr. 19, 1985

[30] Foreign Application Priority Data

| | | |
|---|---|---|
| Apr. 20, 1984 [JP] | Japan | 59-79965 |
| Jul. 25, 1984 [JP] | Japan | 59-154946 |
| Sep. 18, 1984 [JP] | Japan | 59-195471 |
| Sep. 18, 1984 [JP] | Japan | 59-195472 |
| Oct. 16, 1984 [JP] | Japan | 59-216560 |
| Jan. 17, 1985 [JP] | Japan | 60-6519 |
| Mar. 5, 1985 [JP] | Japan | 60-42930 |
| Mar. 5, 1985 [JP] | Japan | 60-42931 |

[51] Int. Cl.$^4$ .......... A61K 7/13; C07C 87/64
[52] U.S. Cl. .......... 8/426; 8/405; 8/406; 8/421; 8/650; 8/651; 8/653; 564/428
[58] Field of Search .......... 8/405, 406, 421, 426; 564/428

[56] References Cited

U.S. PATENT DOCUMENTS

| | | | |
|---|---|---|---|
| 2,508,203 | 5/1950 | Weber | 8/400 |
| 3,041,244 | 6/1962 | Feit et al. | 8/408 |
| 3,251,744 | 5/1966 | Brunner | 8/405 |
| 3,516,778 | 6/1970 | Brunner | 8/405 |

FOREIGN PATENT DOCUMENTS

| | | |
|---|---|---|
| 889813 | 2/1962 | United Kingdom. |
| 1097271 | 1/1968 | United Kingdom. |
| 2110722 | 6/1983 | United Kingdom. |
| 2110723 | 6/1983 | United Kingdom. |

*Primary Examiner*—A. Lionel Clingman
*Attorney, Agent, or Firm*—Sprung, Horn, Kramer & Woods

[57] ABSTRACT

A naphthalene derivative having the general formula:

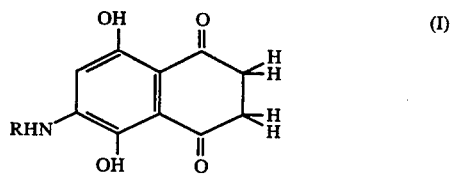

wherein R represents hydrogen, an alkyl group having 1 to 8 carbon atoms, an $R^1O(CH_2)_n$ group, or a benzyl group, $R^1$ represents hydrogen or a lower alkyl group, and n represents an integer of 2 or 3.

This compound in the leuco state can be stably isolated and can produce a strong and fast color upon oxidation under moderate conditions. This compound can be advantageously included in a hair dye composition, which is capable of stably and safely dyeing hair with a good and stable color under moderate conditions.

9 Claims, No Drawings

5,8-DIHYDROXY NAPHTHALENE-1,4-DIONE DERIVATIVE AND A HAIR DYE COMPOSITION CONTAINING THE SAME

BACKGROUND OF THE INVENTION

1. Field of the Invention

The present invention relates to a novel naphthalene derivative, useful as a dye or pigment or an intermediate thereof. The present invention also relates to a hair dye composition containing the novel naphthalene derivative, which is capable of dyeing hair with good color fastness.

2. Description of the Related Art

Conventional vat dyes for use in dyeing fibers are those which are first converted, with reducing agents, to the colorless leuco states in dyeing baths and then air oxidized in the baths, while dipping fibers therein, to insoluble colored states adsorbed on the dipped fibers. For example, indigo, a known and typical vat dye, has the following chemical structure (II):

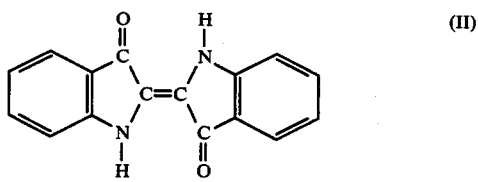

when indigo is used in dyeing, the fibers to be dyed are dipped in a dyeing solution containing the indigo, an alkaline compound, and a reducing compound. The indigo is in the leuco state having the following formula (III) under these conditions.

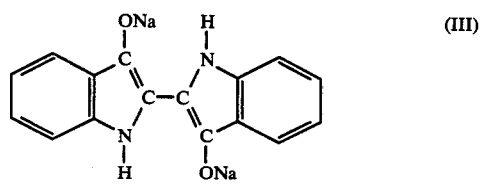

In addition to indigo, other dyes such as indanthrene dyes and anthraquinone dyes are also known as vat dyes. These dyes are also used to color or dye fabrics by a mechanism similar to that mentioned above.

The above-mentioned leuco states are very unstable and are immediately oxidized upon contact with air. Accordingly, it is necessary, in practice, to incorporate a large amount of a reducing agent in a dyeing bath. This incorporation, however, produces severe conditions in the fibers to be dyed. Furthermore, the reduction of indigo under alkaline conditions causes damage to the fibers.

It is well-known in the art that, although Helindon Yellow R developed by Cassella Co., comprised of naphthoquinone dyes having a condensed carbazole ring are yellow vat dyes suitable for dyeing wool, it has not been placed on the market because of the disadvantage that a strong alkaline bath is required in the reduction step. Use of the sulfuric acid ester of indigo in the leuco state has been proposed. However, since sulfuric acid ester is too stable, it is impossible to obtain the desired color unless a strong oxidizing agent such as potassium permanganate is used. The use of such a strong oxidizing agent also is likely to cause damage to the fibers. In addition, the improvements in the coloring power of conventional vat dyes are desired in the art because this coloring power is still unsatisfactory.

On the other hand, dye components used mainly in conventional hair dyes are oxidation dyes, which are capable of dyeing or coloring hair by oxidatively polymerizing, for example, a developer such as p-phenylenediamine, p-tolylenediamine, or other benzene derivative, and a coupler such as resorcinol, m-aminophenol, or m-phenylenediamine in the presence of hydrogen peroxide and ammonia. Similarly, it is known in the art as described in, for example, German Pat. No. 3016905, that oxidation dyes composed of indole and pyrimidine derivatives having dyeing mechanisms similar to the above-mentioned oxidation dyes are used in hair dyes.

Furthermore, various hair dyes containing, as a dye component, quinone type coloring agents have been proposed in, for example, German Offenlegungsschrift Nos. 3244452 and 3244454 and French Pat. No. 1567219. However, these coloring agents are used as a direct dye for dyeing hair but are used only to provide a certain shade to the air, e.g., tinting or color rinsing.

It has also been reported that botanical extracts, for example, certain extracted components derived from henna are used or dyeing hair. However, the coloring power of these extracts still not as satisfactory as desired.

Although the above-mentioned oxidation dyes are capable of imparting a good dyeing action to hair, the reactions involved in the course of the dyeing are extremely complicated and produce various kinds of oxidation products, since the coloring occurs through the above-mentioned oxidative polymerization. For this reason, it may often occur that the resultant color is remarkably varied, depending upon very slight differences in the dyeing conditions, even when the same dye is used. In addition, since these dyes are very unstable in air or in solvents (e.g., these dyes are susceptible to oxidation or oxidative polymerization), care must be taken during the handling thereof. For example, these dyes should be stored under an oxygen free atmosphere, for example, a nitrogen atmosphere. Furthermore, these dyes sometimes cause damage to the skin or hair when applied, depending upon individual reactions to the dye. Therefore, there is a strong need in the art for the development of new types of hair dyes which have a satisfactory coloring power, good color stability when applied, good storage stability, and a high safety level.

SUMMARY OF THE INVENTION

Accordingly, the objects of the present invention are to eliminate the above-mentioned disadvantages and problems in the arts and to provide a novel naphthalene derivative which is capable of being stably isolated in the form of the leuco state and also of producing a strong and fast color upon oxidation under moderate conditions.

Another object of the present invention is to provide a hair dye composition, which is capable of stably dyeing hair under moderate conditions with a good and stable color and which has a high safety level and excellent storage stability.

Other objects and advantages of the present invention will be apparent from the following description.

In accordance with the present invention, there is provided a naphthalene derivative having the general formula:

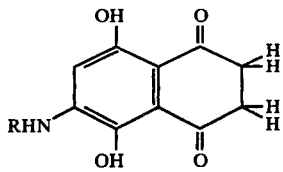

wherein R represents hydrogen, an alkyl group having 1 to 8 carbon atoms, an $R^1O(CH_2)_n$ group, or a benzyl group, $R^1$ represents hydrogen or a lower alkyl group, having 1 to 5 carbon atoms, typically a methyl or ethyl group, and n represents an integer of 2 or 3.

In accordance with the present invention, there is also provided a hair dye composition comprising the above-mentioned naphthalene derivative having the general formula (I).

DESCRIPTION OF THE PREFERRED EMBODIMENTS

The naphthalene derivatives having the above-mentioned general formula (I) are novel compounds hitherto undisclosed in any literature. The naphthalene derivatives having the general formula (I) can be prepared from the known compound, naphthazarin (i.e., 5,8-dihydroxy-1,4-naphthoquinone) having the formula (IV) as follows.

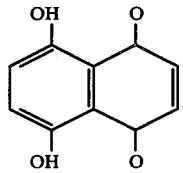

That is, naphthazarin is first reacted with an alkylamine $RNH_2$, wherein R is the same as defined above, to prepare an intermediate compound having the formula (V):

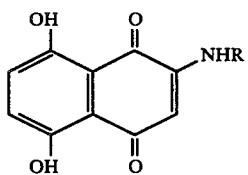

this reaction can be carried out in an organic solvent (e.g., ethanol, dimethylformamide), preferably at a low temperature (e.g., room temperature or less). Although there is no special limitation in the reaction mole ratio of naphthazarin to the alkylamine, the preferable ratio is 1:5 to 25.

The intermediate compound (V) obtained above can be reduced to form the desired naphthalene derivative (I). For example, the reduction can be carried out in the presence of an alkaline compound such as potassium hydroxide, sodium hydroxide or sodium carbonate by using an appropriate reducing agent such as sodium dithionite in water, an alcohol, or an aqueous alcohol. The reduction also can be carried out in the presence of zinc in an aqueous hydrochloric acid. The reaction is typically carried out at room temperature to a reflux temperature for 1 to 5 hours under anaerobic conditions.

Example of the naphthalene derivative according to the present invention are as follows:
- 6-Amino-2,3-dihydro-5,8-dihydroxynaphthalene-1,4-dione (i.e., R=H);
- 6-Methylamino-2,3-dihydro-5,8-dihydroxynaphthalene-1,4-dione (i.e., $R=CH_3$);
- 6-Ethylamino-2,3-dihydro-5,8-dihydroxynaphthalene-1,4-dione (i.e., $R=C_2H_5$);
- 6-Propylamino-2,3-dihydro-5,8-dihydroxynaphthalene-1,4-dione (i.e., $R=C_3H_7$);
- 6-Butylamino-2,3-dihydro-5,8-dihydroxynaphthalene-1,4-dione (i.e., $R=C_4H_9$);
- 6-Pentylamino-2,3-dihydro-5,8-dihydroxynaphthalene-1,4-dione (i.e., $R=C_5H_{11}$);
- 6-Hexylamino-2,3-dihydro-5,8-dihydroxynaphthalene-1,4-dione (i.e., $R=C_6H_{13}$);
- 6-Heptylamino-2,3-dihydro-5,8-dihydroxynaphthalene-1,4-dione (i.e., $R=C_7H_{15}$);
- 6-Octylamino-2,3-dihydro-5,8-dihydroxynaphthalene-1,4-dione (i.e., $R=C_8H_{17}$);
- 6-(2'-Hydroxyethyl- or 3'-hydroxypropylamino)-2,3-dihydro-5,8-dihydroxynaphthalene-1,4-dione (i.e., $R^1=H$, n=2 or 3);
- 6-(2'-Alkoxyethyl- or 3'-alkoxypropylamino-2,3-dihydro-5,8-dihydroxynaphthalene-1,4-dione (i.e., $R^1=$a lower alkyl group, n=2 or 3); and
- 6-Benzylamino-2,3-dihydro-5,8-dihydroxynaphthalene-1,4-dione (i.e., R=benzyl)

The naphthalene derivative (I) according to the present invention can be isolated in the leuco state from the reaction mixture can be stably stored, can dye fibers with a good color in a dyeing bath even without the use of a specific oxidizing agent. Especially, the naphthalene derivative according to the present invention can exhibit a practically acceptable coloring power even at an approximately 0.1% by weight bath concentration under room temperature, although a 5% by weight or more bath concentration is generally required, at an elevated temperature, for obtaining satisfactory dyeing in the case of conventional vat dyes.

When fibers are dyed by the present naphthalene derivative, approximately 0.7% to 2.0% by weight of ammonia can be advantageously included in a dyeing bath to dye the fibers with a good color.

As mentioned above, the naphthalene derivative according to the present invention can be advantageously formulated into a hair dye composition, which is capable of stably dyeing hair with a good and fast color under moderate conditions. Although there is no specific limitation in the concentration of the naphthalene derivative in the hair dye, the naphthalene derivative is preferably included in the hair dye at a concentration of 0.01% by weight or more, more preferably 0.01% to 5% by weight, and most preferably 0.05% to 2% by weight. The use of too large an amount of the naphthalene derivative is wasteful from the economical point of view. The increase in the coloring power of the naphthalene derivative becomes gradually flat above a 2% by weight bath concentration.

The hair dye composition according to the present invention can include, in addition to the naphthalene derivative, any conventional ingredients. Examples of such ingredients are 10% to 20% by weight of a surfactant (e.g., polyoxyethylene monostearate, polyoxyethylene sorbitan monooleate, and cetyl alcohol), 10% to 15% by weight of an alcohol (e.g., isopropyl alcohol and ethyl alcohol), 10% to 15% by weight of a humectant (e.g., glycerol and ethylene glycol), and a balance (or remainder) of water. The hair dye composition according to the present invention may also contain any optional ingredients generally used in the formulation of conventional hair dye compostions. Examples of such ingredients are organic acids (e.g., oleic acid), coloring agents and perfumes.

As mentioned above, conventional vat dyes for coloring fibers are first converted with a reducing agent in a dyeing bath to the leuco state and the dyes in the leuco state are air oxidized while immersing fibers in the dyeing bath, to form colored products adsorbed on the fibers. For example, in the case of indigo, which is a typical vat dye, fibers are immersed in a bath solution containing indigo, an alkaline compound, and a reducing agent. Under these conditions, the indigo is present in the leuco state. It is believed that the indigo is then subjected to air oxidation to become a colored product, which is simultaneously adhered to the fibers. However, as mentioned above, indigo in the leuco state is very unstable so that the leuco state indigo is immediately oxidized upon contact with air unless a large amount of a reducing agent is present in the bath. However, the presence of a large amount of a reducing agent provides severe conditions for the fibers to be dyed. In addition, since the reduction is carried out under strong alkaline conditions, further damage is caused to the fibers.

When indigo in the leuco state is converted to the sulfuric acid ester, the stability in the leuco state is increased. However, since the sulfuric acid ester is too stable, the desired coloring cannot be obtained unless a strong oxidizing agent such as potassium permanganate is used. The use of such a strong oxidizing agent is not desirable for fibers.

For the above-mentioned reasons conventional vat dyeing techniques cannot be directly applied to hair dyeing process. However, the naphthalene derivatives according to the present invention have appropriate stability. That is, the naphthalene derivatives having the general formula (I) in the leuco state can be isolated and can be oxidized under moderate conditions to produce a strong and fast color. Therefore, the naphthalene derivatives according to the present invention are ideal for use as dyes for dyeing hair.

Vat dyes have not been previously to hair dyeing. Thus, the present inventors have first synthesized and isolated novel naphthalene derivatives in the leuco state, which are capable of providing a good color without using a reducing agent in a dyeing bath and are capable of being advantageously applied for dyeing hair. Furthermore, according to the present invention, a practically acceptable coloring power can be exhibited even at an extremely low concentration of about 0.1% by weight in the bath and even at a low temperature of 40° C. or less, although the desired color cannot be obtained at a concentration of 5% by weight or more and at an elevated temperature in the case of conventional vat dyes. Moreover, the hair dye composition according to the present invention neither damages the hair nor irritates the skin.

Furthermore, the naphthalene derivatives according to the present invention can also be utilized, in addition to dyestuffs and hair dyeing agents, as pigments for liquid crystals, coloring agnets for recording media such as photo discs, and other coloring agnets or pigments.

EXAMPLES

The present invention will now be further illustrated by, but is by no means limited to, the following Examples, wherein "percents" are all by weight unless otherwise specified.

Synthetic Example 1

Synthesis of 6-Butylamino-2,3-dihydro-5,8-dihydroxynaphthalene-1,4-dione (1) Synthesis of Intermediate Product A 80 ml amount of 10 mmol of naphthazarin in ethanol solution was gradually added to 200 mmol of n-butylamine at a temperature of 0° C. while stirring. After the completion of the reaction, the reaction mixture was poured into a dilute hydrochloric acid solution. The precipitates thus formed were filtered and the filtered product was dried in vacuo. The dried product was subjected to column chromatography in which silica gel and chloroform were used as a packing and solvent, respectively.

Thus, the desired product was fractionated to obtain 1.47 g of the desired crystalline intermediate product (yield=55.8%). This product was confirmed to be 2-butylamino-5,8-dihydroxynaphthoquinone from the follwoing analytical data:

Mass spectrum: $M^+ = 261$
Elementary analysis:

|  | C | H | N |
|---|---|---|---|
| Calculated: | 64.36 | 5.79 | 5.36 |
| Found: | 64.17 | 5.78 | 5.31 |

NMR spectrum (CDCl$_3$, δ, ppm):
$^1$H—NMR: 13.58 (1H, OH, S), 11.97 (1H, OH, S), 7.03-7.30 (2H, arom., q), 6.15 (1H, NH, broad), 5.75 (1H, quinone, s), 0.90-3.40 (9H, butyl group)
$^{13}$C—NMR: the chemical shifts of carbonyl carbon: 187.0, 183.8 ppm The similar results can be obtained when benzene is used as a column chromatography solvent.

(2) Synthesis of Desired Product

A 0.902 g amount of 2-butylamino-5,8-dihydroxy naphthoquinone obtained above was dissolved, together with 0.856 g of sodium carbonate and 3.457 g of sodium dithionite, in 60 ml of 50% aqueous ethanol. The mixture was allowed to react at a temperature of 80° C. for 3 hours while stirring under argon atmosphere. After the completion of the reaction, the resultant crystalline product was filtered and washed with degassed water and dried in vacuo. Thus, 0.477 g of the desired product was obtained (yield=52.4%).

The analytical data of the resultant product were as follows:

Mass spectrum: $M^+ = 263$
Elementary analysis:

|  | C | H | N |
|---|---|---|---|
| Calculated: | 63.87 | 6.51 | 5.32 |
| Found: | 63.68 | 6.54 | 5.30 |

NMR spectrum (CDCl$_3$, δ, ppm):
$^1$H—NMR: 12.95 (1H, OH, S), 12.50 (1H, OH, S), 6.21 (1H, arom., S), 5.30 (1H, NH, broad), 2.74 (4H, —(CH$_2$)$_2$—, S), 0.90–3.40 (9H, butyl group)
$^{13}$C—NMR: the chemical shifts of carbonyl carbon; 203.0, 196.9 ppm The resultant product is confirmed to be the desired 6-butylamino-2,3-dihydro-5,8-dihydroxynaphthalene-1,4-dione for the reason that a methyl or methylene group is considered to be present in the position adjacent to a carbonyl group because the chemical shift of the carbonyl group in $^{13}$C—NMR spectrum is observed in the lower magnetic field side when compared with that of the corresponding quinones.

Synthetic Example 2

Synthesis of 6-Pentylamino-2,3-dihydro-5,8-dihydroxynaphthalene-1,4-dione (1) Synthesis of Intermediate Product A 80 ml amount of an ethanol solution containing 10 mmol of naphthazarin was gradually added to 200 mmol of n-pentylamine at temperature of 0° C. to 2° C. for 3.5 hours while stirring. After the completion of the reaction, the reaction mixture was poured into a dilute hydrochloric acid solution. The precipitates thus formed were filtered and the filtered product was dried in vacuo. The dried product was subjected to column chromatography in which silica gel and benzene were used as a packing and solvent, respectively.

Thus, the desired product was fractionated to obtain 1.230 g of the desired crystalline intermediate product (yield=44.5%). The product was recrystallized from ethanol. This product was confirmed to be 2-pentylamino-5,8-dihydroxynaphthoquinone from the following analytical data:
Mass spectrum: M$^+$=275
Elementary analysis:

|  | C | H | N |
|---|---|---|---|
| Calculated: | 65.44 | 6.22 | 5.09 |
| Found: | 65.41 | 6.25 | 5.08 |

NMR spectrum (CDCl$_3$, δ, ppm):
$^1$H—NMR: 13.37 (1H, OH, S), 11.81 (1H, OH, S), 7.01–7.30 (2H, arom., q), 6.07 (1H, NH, broad), 5.66 (1H, quinone, s), 0.90–3.29 (11H, pentyl group)
$^{13}$C—NMR: the chemical shifts of carbonyl carbon; 187.0, 183.8 ppm (2) Synthesis of Desired Product A 600 mg amount of 2-pentylamine-5,8-dihydroxy naphthoquinone obtained above was dissolved, together with 600 mg of sodium carbonate and 1600 mg of sodium dithionite, in 35 ml of aqueous ethanol (ethanol:water=15:20). The mixture was allowed to react at a reflux temperature for 3 hours while stirring under argon atmosphere. After the completion of the reduction was confirmed by the change of the reaction mixture to yellowish brown, the reaction mixture was cooled to room temperature. The resultant crystalline product was filtered and thoroughly washed with degassed water and dried in vacuo. All the operations were carried out under argon atmosphere. Thus, 461 mg of the desired product was obtained (yield=76.8%).

The product was recrystallized from ethanol under argon atmosphere.
The analytical data of the resultant product were as follows:
Mass spectrum: M$^+$=277
Elementary analysis:

|  | C | H | N |
|---|---|---|---|
| Calculated: | 64.97 | 6.91 | 5.05 |
| Found: | 64.97 | 6.92 | 5.01 |

NMR spectrum (CDCl$_3$, δ, ppm):
$^1$H—NMR: 12.94 (1H, OH, S), 12.49 (1H, OH, S), 6.21 (1H, arom., S), 5.33 (1H, NH, broad), 2.95 (4H, —(CH$_2$)$_2$—, S), 0.90–3.30 (9H, pentyl group)
$^{13}$C—NMR: the chemical shifts of carbonyl carbon; 203.0, 196.9 ppm The resultant product is confirmed to be the desired 6-pentylamino-2,3-dihydro-5,8- dihydroxynaphthalene-1,4-dione for the reason that a methyl or methylene group is considered to be present in the position adjacent to a carbonyl group because the chemical shift of the carbonyl group in $^{13}$C—NMR spectrum is observed in the lower magnetic field side when compared with that of the corresponding quinones.

Synthetic Example 3

Synthesis of 6-Hexylamino-2,3-dihydro-5,8-dihydroxynaphthalene-1,4-dione (1) Synthesis of Intermediate Product A 80 ml amount of an ethanol solution containing 10 mmol of of naphthazarin was gradually added to 200 mmol of n-hexylamine at a temperature of 2° C. to 4° C. for 2.5 hours while stirring. After the completion of the reaction, the reaction mixture was poured into a dilute hydrochloric acid solution. The precipitates thus formed were filtered and the filtered product was dried in vacuo. The dried product was subjected to column chromatography in which silica gel and benzene were used as a packing and solvent, respectively.

Thus, the desired product was fractionated to obtain 1.381 g of the desired crystalline intermediate product (yield=47.5%). The product was recrystallized from ethanol. This product was confirmed to be 2-hexylamino-5,8-dihydroxynaphthoquinone from the follwoing analytical data:
Mass spectrum: M$^+$=289
Elementary analysis:

|  | C | H | N |
|---|---|---|---|
| Calculated: | 66.42 | 6.62 | 4.84 |
| Found: | 66.42 | 6.62 | 4.88 |

NMR spectrum (CDCl$_3$, δ, ppm):
$^1$H—NMR: 13.37 (1H, OH, S), 11.81 (1H, OH, S), 7.00–7.30 (2H, arom., q), 6.07 (1H, NH, broad), 5.65 (1H, quinone, s), 0.90–3.29 (13H, hexyl group)
$^{13}$C—NMR: the chemical shifts of carbonyl carbon; 187.0, 183.7 ppm (2) Synthesis of Desired Product A 300 mg amount of 2-hexylamino-5,8-dihydroxy naphthoquinone obtained above was dissovled, together with 300 mg of sodium carbonate and 900 mg of sodium dithionite, in 20 ml of aqueous ethanol (ethanol:-water=10:10). The mixture was allowed to react at a reflux temperature for 1 hour while stirring under argon atmosphere. After the completion of the sufficient reduction was confirmed by the change of the rection mixture to yellowish brown, the reaction mixture was cooled to room temperature. The resultant crystalline product was filtered and washed with degassed water and dried in vacuo. Thus, 220 mg of the desired product was obtained (yield=72.8%). The product was recrystallized from ethanol under argon atmosphere.

The analytical data of the resultant product were as follows:

Mass spectrum: $M^+ = 291$
Elementary analysis:

|  | C | H | N |
|---|---|---|---|
| Calculated: | 65.96 | 7.26 | 4.81 |
| Found: | 65.82 | 7.25 | 4.57 |

NMR spectrum (CDCl$_3$, δ, ppm):
$^1$H—NMR: 12.94 (1H, OH, S), 12.49 (1H, OH, S), 6.21 (1H, arom., S), 5.33 (1H, NH, broad), 2.94 (4H, —(CH$_2$)$_2$—, S), 0.91–3.35 (13H, hexyl group)
$^{13}$C—NMR: the chemical shifts of carbonyl carbon; 203.0, 196.9 ppm From the above analytical data, the formation of the desired 6-hexylamino-2,3-dihydro-5,8-dihydroxynaphthalene-1,4-dione was confirmed although several tautomers are present.

Synthetic Example 4

Synthesis of 6-Heptylamino-2,3-dihydro-5,8-dihydroxynaphthalene-1,4-dione (1) Synthesis of Intermediate Product A 80 ml amount of an ethanol solution containing 10 mmol of naphthazarin was gradually added to 200 mmol of n-heptylamine at a temperature of 0° C. to 2° C. while stirring. After the completion of the reaction, the reaction mixture was poured into a dilute hydrochloric acid solution. The precipitates thus formed were filtered and the filtered product was dried in vacuo. The dried product was subjected to column chromatography in which silica gel and benzene were used as a packing and solvent, respectively.

Thus, the desired product was fractionated to obtain 1.438 g of the desired crystalline intermediate product (yield=43.2%). The product was recrystallized from ethanol. This product was confirmed to be 2-heptylamino-5,8-dihydroxynaphthoquinone from the follwoing analytical data:

Mass spectrum: $M^+ = 303$
Elementary analysis:

|  | C | H | N |
|---|---|---|---|
| Calculated: | 67.31 | 6.98 | 4.62 |
| Found: | 67.13 | 6.98 | 4.59 |

NMR spectrum (CDCl$_3$, δ, ppm):
$^1$H—NMR: 13.37 (1H, OH, S), 11.82 (1H, OH, S), 7.02–7.31 (2H, arom., q), 6.05 (1H, NH, broad), 5.67 (1H, quinone, s), 0.90–3.30 (9H, heptyl group)
$^{13}$C—NMR: the chemical shifts of carbonyl carbon; 187.1, 183.8 ppm (2) Synthesis of Desired Product A 200 mg amount of 2-heptylamino-5,8-dihydroxynaphthoquinone obtained above was dissovled, together with 200 mg of sodium carbonate and 700 mg of sodium dithionite, in 30 ml of aqueous ethanol (ehtanol:-water=10:20). The mixture was allowed to react at a reflux temperature for 1 hour while stirring under argon atmosphere. After the completion of the sufficient reduction was confirmed by changing the reaction mixture to yellowish brown, the reaction mixture was cooled to room temperature. The resultant crystalline product was filtered and washed with degassed water and dried in vacuo. All the operations were carried out under argon atmosphere. Thus, 98 mg of the desired product was obtained (yield=48.7%). The product was recrystallized from ethanol.

The analytical data of the resultant product were as follows:

Mass spectrum: $M^+ = 305$
Elementary analysis:

|  | C | H | N |
|---|---|---|---|
| Calculated: | 66.86 | 7.59 | 4.59 |
| Found: | 67.07 | 7.81 | 4.20 |

NMR spectrum (CDCl$_3$, δ, ppm):
$^1$H—NMR: 12.94 (1H, OH, S), 12.49 (1H, OH, S), 6.21 (1H, arom., S), 5.32 (1H, NH, broad), 2.94 (4H, —(CH$_2$)$_2$—, S), 0.89–3.31 (15H, heptyl group)
$^{13}$C—NMR: the chemical shifts of carbonyl carbon; 203.0, 196.9 ppm The resultant product is confirmed to be the desired 6-heptylamino-2,3-dihydro-5,8-dihydroxynaphthalene-1,4-dione from the above analytical data although several tautomers are present.

Synthetic Example 5

Synthesis of 6-Octylamine-2,3-dihydro-5,8-dihydroxynaphthalene-1,4-dione (1) Synthesis of Intermediate Product A 80 ml amount of an ethanol solution containing 10 mml of naphthazarin was gradually added to 200 mmol of n-octylamine at a temperature of 0° C. to 2° C. for 3.5 hours while stirring. After the completion of the reaction, the reaction mixture was poured into a dilute hydrochloric acid solution. The precipitates thus formed were filtered and the filtered product was dried in vacuo. The dried product was subjected to column chromatography in which silica gel and benzene were used as a packing and solvent, respectively.

Thus, the desired product was fractionated to obtain 1.591 g of the desired crystalline intermediate product (yield=50.0%). The product was recrystallized from ethanol. This product was confirmed to be 2-octylamino-5,8-dihydroxynaphthoquinone from the follwoing analytical data:

Mass spectrum: $M^+ = 317$
Elementary analysis:

|  | C | H | N |
|---|---|---|---|
| Calculated: | 68.12 | 7.30 | 4.41 |
| Found: | 68.10 | 7.29 | 4.38 |

NMR spectrum (CDCl$_3$, δ, ppm):
$^1$H—NMR: 13.38 (1H, OH, S), 11.83 (1H, OH, S), 7.02-7.31 (2H, arom., q), 6.07 (1H, NH, broad), 5.67 (1H, quinone, s), 0.89-3.30 (17H, octyl group)
$^{13}$C—NMR: the chemical shifts of carbonyl carbon; 187.0, 183.8 ppm (2) Synthesis of Desired Product A 600 mg amount of 2-octylamino-5,8-dihydroxynaphthoquinone obtained above was dissolved, together with 600 mg of sodium carbonate and 1600 mg of sodium dithionite, in 30 ml of aqueous ethanol (ethanol:water=15:15). The mixture was allowed to react at a reflux temperature for 4 hours while stirring under argon atmosphere. After the completion of the sufficient reduction was comfirmed by the change of the reaction mixture of yellowish brown, the reaction mixture was cooled to room temperature. The resultant crystalline product was filtered and thoroughly washed with degassed water and dried in vacuo. All the operations were carried out under argon atmosphere. Thus, 418 mg of the desired product was obtained (yield=69.2%). The product was recrystallized from ethanol.

The analytical data of the resultant product were as follows:
Mass spectrum: M$^+$=319
Elementary analysis:

|  | C | H | N |
|---|---|---|---|
| Calculated: | 67.69 | 7.89 | 4.39 |
| Found: | 67.48 | 7.94 | 4.26 |

NMR spectrum (CDCl$_3$, δ, ppm):
$^1$H—NMR: 12.95 (1H, OH, S), 12.50 (1H, OH, S), 6.21 (1H, arom., S), 5.32 (1H, NH, broad), 2.95 (4H, —(CH$_2$)$_2$—, S), 0.90-3.36 (15H, octyl group)
$^{13}$C—NMR: the chemical shifts of carbonyl carbon; 203.0, 196.9 ppm The resultant product is confirmed to be the desired 6-octylamino-2,3-dihydro-5,8-dihydroxy naphthalene-1,4-dione from the above analytical data although several tautomers are present.

Synthetic Example 6

Synthesis of 6-benzylamino-2,3-dihydro-5,8-dihydroxynaphthalene-1,4-dione (1) Synthesis of Intermediate Product A 80 ml amount of an ethanol solution of 10 mmol naphthazarin was gradually added to 200 mmol of benzylamine at a temperature of 0° C. to 2° C. for 3.5 hours while stirring. After the completion of the reaction, the reaction mixture was poured into a dilute hydrochloric acid solution. The precipitates thus formed were filtered and the filtered product was dried in vacuo. The dried product was subjected to column chromatography in which silica gel and benzene were used as a packing and solvent, respectively.

Thus, the desired product was fractionated to obtain 1.257 g of the desired crystalline intermediate product (Yield=42.3%). The product was recrystallized from ethanol. This product was confirmed to be 2-benzylamino-5,8-dihydroxynaphthoquinone from the follwoing analytical data:
Mass spectrum: M$^+$=295

Elementary analysis:

|  | C | H | N |
|---|---|---|---|
| Calculated: | 69.15 | 4.44 | 4.74 |
| Found: | 69.11 | 4.44 | 4.68 |

NMR spectrum (CDCl$_3$, δ, ppm):
$^1$H—NMR: 13.28 (1H, OH, S), 11.83 (1H, OH, S), 7.35 (5H, arom., like S), 7.03-7.26 (2H, arom., q), 6.39 (1H, NH, broad), 5.72 (1H, quinone, s), 4.36-4.42 (2H, CH$_2$ph, d)
$^{13}$C—NMR: the chemical shifts of carbonyl carbon; 187.2, 183.7 ppm (2) Synthesis of Desired Product A 400 mg amount of 2-benzylamino-5,8-dihydroxynaphthoquinone obtained above was dissovled, together with 400 mg of sodium carbonate and 1200 mg of sodium dithionite, in 30 ml of water. The mixture was allowed to react at a reflux temperature for 3 hours while stirring under argon atmosphere. After the completion of the sufficient reduction was confirmed by changing the reaction mixture to yellowish brown, the reaction mixture was cooled to room temperature. The resultant crystalline product was filtered and thoroughly washed with degassed water and dried in vacuo. All the operations were carried out under argon atmosphere. Thus, 355 mg of the desired product was obtained (yield=88.8%). The product was recrystallized from ethanol under argon atmosphere.

The analytical data of the resultant product were as follows:
Mass spectrum: M$^+$=297
Elementary analysis:

|  | C | H | N |
|---|---|---|---|
| Calculated: | 68.68 | 5.09 | 4.71 |
| Found: | 68.50 | 5.00 | 4.62 |

NMR spectrum (CDCl$_3$, δ, ppm):
$^1$H—NMR: 12.85 (1H, OH, S), 12.50 (1H, OH, S), 7.32 (5H, arom., S), 6.22 (1H, arom., s), 5.71 (1H, NH, broad), 4.38-4.44 (2H, CH$_2$ph,), 2.93 (4H, —(CH$_2$)$_2$—, S),
$^{13}$C—NMR: the chemical shifts of carbonyl carbon; 202.9, 197.2 ppm The resultant product is confirmed to be the desired 6-benzylamino-2,3-dihydro-5,8-dihydroxynaphthalene-1,4-dione for the reason that a methyl or methylene group is considered to be present in the position adjacent to a carbonyl group because the chemical shift of the carbonyl group in $^{13}$C—NMR spectrum is observed in the remarkably lower magnetic field side when compared with that of the corresponding quinones.

Synthetic Example 7

Synthesis of 6-(2'-hydroxyethylamino)-2,3-dihydro-5,8-dihydroxynaphthalene-1,4-dione (1) Synthesis of Intermediate Product A 80 ml amount of an ethanol solution containing 10 mmol naphthazarin was gradually added to 200 mmol of 2-aminoethanol at a temperature of 0° C. to 2° C. while stirring. After the completion of the reaction, the reaction mixture was poured into a dilute hydrochloric acid solution. The precipitates thus formed were filtered off and the filtered product was dried in vacuo. The dried product was subjected to column chromatography in which silica gel and benzene were used as a packing and solvent, respectively.

Thus, the desired product was fractionated to obtain 1.571 g of the desired crystalline intermediate product (yield=62.7%). The product was recrystallized from ethanol. This product was confirmed to be 2-(2'-hydroxyethylamino)-5,8-dihydroxynaphthoquinone from the follwoing analytical data:
Mass spectrum: M+=249
Elementary analysis:

|  | C | H | N |
|---|---|---|---|
| Calculated: | 57.83 | 4.45 | 5.62 |
| Found: | 57.77 | 4.41 | 5.58 |

NMR spectrum (CDCl$_3$, δ, ppm):
$^1$H—NMR: 13.60 (1H, OH, S), 11.65 (1H, OH, S), 7.73 (1H, NH, broad), 7.10–7.40 (2H, arom., m), 5.68 (1H, quinone, s), 4.85 (1H, NH—OH, broad), 3.10–3.70 (4H for ethyl group)
$^{13}$C—NMR: the chemical shifts of carbonyl carbon; 186.1, 183.5 ppm (2) Synthesis of Desired Product A 600 mg amount of 2-(2'-hydroxyethylamino)-5,8-dihydroxynaphthoquinone obtained above was dissovled, together with 600 mg of sodium carbonate and 1600 mg of sodium dithionite, in 35 ml of aqueous ethanol (ethanol:water=15:20). The mixture was allowed to react at a reflux temperature for 3 hours while stirring under argon atmosphere. After the completion of the sufficient reduction was confirmed by the change of the reaction mixture to yellowish brown, the reaction mixture was cooled to room temperature. The resultant crystalline product was filtered and thoroughly washed with degassed water and dried in vacuo. Thus, 450 mg of the desired product was obtained (yield=75.8%). The product was recrystallized from ethanol under argon atmosphere.

The analytical data of the resultant product were as follows:
Mass spectrum: M+=251
Elementary analysis:

|  | C | H | N |
|---|---|---|---|
| Calculated: | 57.37 | 5.22 | 5.58 |
| Found: | 57.33 | 5.28 | 5.64 |

NMR spectrum (DMSO-d$_6$, δ, ppm):
$^1$H—NMR: 13.08 (1H, OH, S), 12.55 (1H, OH, S), 6.59 (1H, NH, broad), 6.31 (1H, arom., S), 4.57 (1H, NH—OH, broad), 2.95 (4H, —(CH$_2$)$_2$—, t), 2.94–3.66 (4H for ethyl group)
$^{13}$C—NMR: the chemical shifts of carbonyl carbon; 203.8, 197.6 ppm Although several tautomers are present, the resultant product is confirmed to be the desired 6-(2'-hydroxyethylamino)-2,3-dihydro-5,8-dihydroxynaphthalene-1,4-dione for the reason that a methyl or methylene group is considered to be present in the position next to a carbonyl group because the chemical shift of the carbonyl group in $^{13}$C—NMR spectrum is observed in the lower magnetic field side when compared with that of the corresponding quinones.

Synthetic Example 8

Synthesis of 6-(2'-methoxyethylamino)-2,3-dihydro-5,8-dihydroxynaphthalene-1,4-dione (1) Synthesis of Intermediate Product A 80 ml amount of an ethanol solution containing 10 mmol naphthazarin was gradually added to 200 mmol of 2-methoxyethanolamine at a temperature of 0° C. to 2° C. for 3.5 hours while stirring. After the completion of the reaction, the reaction mixture was poured into a dilute hydrochloric acid solution. The precipitates thus formed were filtered off and the filtered product was dried in vacuo. The dried product was subjected to column chromatography in which silica gel and benzene were used as a packing and solvent, respectively.

Thus, the desired product was fractionated to obtain 1.6311 g of the desired crystalline intermediate product (yield=61.6%). The product was recrystallized from ethanol. This product was confirmed to be 2-(2'-methoxyethylamino)-5,8-dihydroxynaphthoquinone from the follwoing analytical data:
Mass spectrum: M+=263
Elementary analysis:

|  | C | H | N |
|---|---|---|---|
| Calculated: | 59.31 | 4.98 | 5.32 |
| Found: | 59.38 | 4.97 | 5.32 |

NMR spectrum (DMSO-d$_6$, δ, ppm):
$^1$H—NMR: 13.33 (1H, OH, S), 11.68 (1H, OH, S), 7.78 (1H, NH, broad), 7.12–7.38 (2H, arom., q), 5.76 (1H, quinone, s), 3.28 (3H, OMe, s), 3.30–3.55 (4H for ethyl group)
$^{13}$C—NMR: the chemical shifts of carbonyl carbon; 186.4, 183.6 ppm (2) Synthesis of Desired Product A 1.007 g amount of 2-(2'-methoxyethylamino)-5,8-dihydroxynaphthoquinone obtained above was dissovled, together with 1.017 g of sodium carbonate and 2.500 g of sodium dithionite, in 60 ml of aqueous ethanol (ethanol:water=20:40). The mixture was allowed to react at a reflux temperature for 3 hours while stirring under argon atmosphere. After the completion of the reaction, the resultant crystalline product was filtered and thoroughly washed with degassed water and dried in vacuo. Thus, 900 mg of the desired product was obtained (yield=88.7%). The product was recrystallized from ethanol under argon atmosphere.

The analytical data of the resultant product were as follows:
Mass spectrum: M+=265
Elementary analysis:

|  | C | H | N |
|---|---|---|---|
| Calculated: | 58.86 | 5.70 | 5.28 |
| Found: | 58.85 | 5.58 | 5.21 |

NMR spectrum (DMSO-d$_6$, δ, ppm):
$^1$H—NMR: 13.01 (1H, OH, S), 12.54 (1H, OH, S), 6.58 (1H, NH, broad), 6.31 (1H, arom., s), 3.01 (3H, OMe, s), 2.95 (4H, —(CH$_2$)$_2$—, t), 3.14–3.66 (4H for ethyl group)

$^{13}$C—NMR: the chemical shifts of carbonyl carbon; 203.8, 197.5 ppm

The resultant product is confirmed to be the desired 6-(2'-methoxyethylamino)-2,3-dihydro-5,8-dihydroxynaphthalene-1,4-dione from $^{13}$C—NMR data and other data, although several tautomers are present.

The naphthalene derivatives having substituents of C$_2$H$_5$O(CH$_2$)$_2$, HO(CH$_2$)$_3$, CH$_3$O(CH$_2$)$_3$, and C$_2$H$_5$O(CH$_2$)$_3$ can also be prepared in the same manner as in Synthetic Examples 7 and 8.

Synthetic Example 9

Synthesis of 6-Amino-2,3-dihydro-5,8-dihydroxynaphthalene-1,4-dione (1) Synthesis of Intermediate Product A 80 ml amount of 10 mmol of naphthazarin in ethanol solution was gradually added to 200 mmol of aqueous ammonia at a room temperature while stirring. After the completion of the reaction, the reaction mixture was poured into a dilute hydrochloric acid solution. The precipitates thus formed were filtered and the filtered product was dried in vacuo. The dried product was subjected to column chromatography in which silica gel and chloroform were used as a packing and solvent, respectively.

Thus, the desired product was fractionated to obtain 102.5 mg of the desired crystalline intermediate product (yield=5%). This product was confirmed to be 2-amino-5,8-dihydroxynaphthoquinone from the follwoing analytical data:

Mass spectrum: M$^+$=205
Elementary analysis:

|  | C | H | N |
|---|---|---|---|
| Calculated: | 58.54 | 3.41 | 6.83 |
| Found: | 58.55 | 3.40 | 6.81 |

NMR spectrum (DMSO-d$_6$, δ, ppm):
$^1$H—NMR: 13.59 (1H, OH, S), 11.72 (1H, OH, S), 7.23–7.60 (2H, arom., q), 7.24 (2H, NH$_2$, broad), 5.80 (1H, quinone, s)
$^{13}$C—NMR: the chemical shifts of carbonyl carbon: 187.0, 183.8 ppm The similar results can be obtained when benzene is used as a column chromatography solvent.

(2) Synthesis of Desired Product

A 200 mg amount of 2-amino-5,8-dihydroxynaphthoquinone obtained above was dissovled, together with 200 mg of sodium carbonate and 400 mg of sodium dithionite, in 60 ml of 50% aqueous ethanol. The mixture was allowed to react at a temperature of 80° C. for 3 hours while stirring under argon atmosphere. After the completion of the reaction, the resultant crystalline product was filtered and washed with degassed water and dried in vacuo. Thus, 150 mg of the desired product was obtained (yield=74.3%).

The analytical data of the resultant product were as follows:

Mass spectrum: M$^+$=207
Elementary analysis:

|  | C | H | N |
|---|---|---|---|
| Calculated: | 57.97 | 4.38 | 6.76 |
| Found: | 57.98 | 4.41 | 6.54 |

NMR spectrum (DMSO-d$_6$, δ, ppm):
$^1$H—NMR: 12.96 (1H, OH, S), 12.25 (1H, OH, S), 6.21 (1H, arom., S), 7.58 (2H, NH$_2$, broad), 2.74 (4H, —(CH$_2$)$_2$—, S),
$^{13}$C—NMR: the chemical shifts of carbonyl carbon; 203.0, 196.9 ppm The resultant product is confirmed to be the desired 6-amino-2,3-dihydro-5,8-dihydroxynaphthalene-1,4-dione for the reason that a methyl or methylene group is considered to be present in the position adjacent to a carbonyl group because the chemical shift of the carbonyl group in $^{13}$C—NMR spectrum is observed in the lower magnetic field side when compared with that of the corresponding quinones.

Synthetic Example 10

Synthesis of 6-Propylamino-2,3-dihydro-5,8-dihydroxynaphthalene-1,4-dione (1) Synthesis of Intermediate Product A 80 ml amount of 10 mmol of naphthazarin in ethanol solution was gradually added to 200 mmol of n-propylamine at a temperature of 0° C. for 1 hour while stirring. After the completion of the reaction, the reaction mixture was poured into a dilute hydrochloric acid solution. The precipitates thus formed were filtered and the filtered product was dried in vacuo. The dried product was subjected to column chromatography in which silica gel and chloroform were used as a packing and solvent, respectively.

Thus, the desired product was fractionated to obtain 1.155 g of the desired crystalline intermediate product (yield=46.7%). This product was confirmed to be 2-propylamino-5,8-dihydroxynaphthoquinone from the follwoing analytical data:

Mass spectrum: M$^+$=247
Elementary analysis:

|  | C | H | N |
|---|---|---|---|
| Calculated: | 63.15 | 5.30 | 5.66 |
| Found: | 63.06 | 5.30 | 5.62 |

NMR spectrum (CDCl$_3$, δ, ppm):
$^1$H—NMR: 13.37 (1H, OH, S), 11.82 (1H, OH, S), 7.03–7.31 (2H, arom., q), 6.03 (1H, NH, broad), 5.68 (1H, quinone, s), 0.96–3.29 (7H, propyl group)
$^{13}$C—NMR: the chemical shifts of carbonyl carbon: 187.0, 183.8 ppm The similar results can be obtained when benzene is used as a column chromatography solvent.

(2) Synthesis of Desired Product

A 400 mg amount of 2-propylamino-5,8-dihydroxynaphthoquinone obtained above was dissovled, together with 400 mg of sodium carbonate and 800 mg of sodium dithionite, in 60 ml of 50% aqueous ethanol. The mixture was allowed to react at a temperature of 80° C. for 3 hours while stirring under argon atmosphere. After the completion of the reaction, the resultant crystalline product was filtered and washed with degassed water and dried in vacuo. Thus, 200 mg of the desired product was obtained (yield=49.6%).

The analytical data of the resultant product were as follows:

Mass spectrum: M+ =249
Elementary analysis:

|  | C | H | N |
|---|---|---|---|
| Calculated: | 63.15 | 5.30 | 5.66 |
| Found: | 63.02 | 5.11 | 5.62 |

NMR spectrum (CDCl$_3$, δ, ppm):
$^1$H—NMR: 13.98 (1H, OH, S), 12.35 (1H, OH, S), 6.20 (1H, arom., S), 5.25 (1H, NH, broad), 2.75 (4H, —(CH$_2$)$_2$—, S), 0.90–3.40 (7H, propyl group)
$^{13}$C—NMR: the chemical shifts of carbonyl carbon; 203.0, 196.9 ppm The resultant product is confirmed to be the desired 6-propylamino-2,3-dihydro-5,8-dihydroxynaphthalene-1,4-dione for the reason that a methyl or methylene group is considered to be present in the position adjacent to a carbonyl group because the chemical shift of the carbonyl group in $^{13}$C—NMR spectrum is observed in the lower magnetic field side when compared with that of the corresponding quinones.

Application Example 1

A 20 mg amount of 6-butylamino-2,3-dihydro-5,8-dihydroxynaphthalene-1,4-dione was dissolved in 20 g of water. Wool muslin test samples available from Shikisensya Co. (Japan) were immersed in the solution prepared above in a bath ratio of 1/40. The fibers were dyed at a temperature of 30° C. or 40° C. for 45 minutes while agitating. Thus, the wool muslin was dyed with bright reddish brown.

Furthermore the presence of 0.7% to 2.0% of ammonia in the dyeing bath results in the better dyeing.

The dyed fibers obtained above were washed in 200 cc of water at a temperature of 30° C. for 5 minutes. After drying, the color was measured by Hitachi Color Analyzer Model 607 (available from Hitachi Ltd., Japan). The results were as shown in Table 1.

TABLE 1

| Dyeing temp. (°C.) | Ammonia conc. (%) | H | V | C |
|---|---|---|---|---|
| 30 | 0 | 6.50R | 4.00 | 5.56 |
|  | 0.7 | 6.06R | 4.23 | 5.66 |
|  | 1.0 | 3.41R | 4.21 | 6.44 |
|  | 1.5 | 2.47R | 3.96 | 6.74 |
|  | 2.0 | 2.06R | 3.97 | 6.66 |
| 40 | 0 | 5.02R | 4.12 | 5.81 |
|  | 0.7 | 3.91R | 3.93 | 5.92 |
|  | 1.0 | 1.70R | 3.50 | 6.51 |
|  | 1.5 | 1.21R | 3.45 | 6.70 |
|  | 2.0 | 0.72R | 3.20 | 6.00 |

The color of the untreated test fibers is H (8.59Y), V (7.04), and C (1.65).

Application Example 2

Multi-fiber test samples containing beige acetate fiber and the other white fibers (available from Shikisansya Co., Japan) were dyed in the same manner as in the Application Example 1. The fibers with bright reddish brown color were obtained depending upon the presence or absence of ammonia and the concentration thereof as in Application Example 1.

Application Example 3

A 20 mg amount each of 6-alkylamino-2,3-dihydro-5,8-dihydroxynaphthalene-1,4-dione obtained in Synthesis Examples 2 to 5 was dissolved in 20 g of water. Wool muslin test samples available from Shikisensya Co. (Japan) were immersed in the solution prepared above in a bath ratio of 1/40. The fibers were dyed at a temperature of 30° C. or 40° C. for 45 minutes while agitating. Thus, the wool muslin was dyed with bright reddish brown.

Furthermore the presence of 0.7% to 2.0% of ammonia in the dyeing bath results in the better dyeing.

Application Example 4

Multi-fiber test samples containing 17 types of fibers, i.e., beige acetate fiber and the other white fibers (available from Shikisansya Co., Japan) were dyed in the same manner as in the Application Example 3. The fibers with bright reddish brown color were obtained depending upon the presence or absence of ammonia and the concentration thereof as in Application Example 3.

Application Example 5

A 20 mg amount of 6-benzylamino-2,3-dihydro-5,8-dihydroxynaphthalene-1,4-dione obtained in Synthetic Example 6 was dissolved in 20 g of water. Wool muslin test samples available from Shikisensya Co. (Japan) were immersed in the solution prepared above in a bath ratio of 1/40. The fibers were dyed at a temperature of 30° C. or 40° C. for 45 minutes while agitating. Thus, the wool muslin was dyed with bright reddish brown.

Furthermore the presence of 0.7% to 2.0% of ammonia in the dyeing bath results in the better dyeing.

Application Example 6

Multi-fiber test samples containing 17 types of fibers, i.e., beige acetate fiber and the other white fibers (available from Shikisansya Co., Japan) were dyed in the same manner as in the Application Example 5. The fibers with bright reddish brown color were obtained depending upon the presence or absence of ammonia and the concentration thereof as in Application Example 5.

Application Example 7

A 20 mg amount of 6-(2'-hydroxyethyl- or 2'-ethoxypropylamino)-2,3-dihydro-5,8-dihydroxynaphthalene-1,4-dione was dissolved in 20 g of water. Wool muslin test samples available from Shikisensya Co. (Japan) were immersed in the solution prepared above in a bath ratio of 1/40. The fibers were dyed at a temperature of 30° C. or 40° C. for 45 minutes while agitating. Thus, the wool muslin was dyed with bright reddish brown in each case, although minor difference was observed depending upon the difference in the substituents.

Furthermore the presence of 0.7% to 2.0% of ammonia in the dyeing bath results in the better dyeing.

Application Example 8

Multi-fiber test samples containing 17 types of fibers, i.e., beige acetate fiber and the other white fibers (available from Shikisansya Co., Japan) were dyed in the same manner as in the Application Example 7. The fibers with bright reddish brown color were obtained depending upon the presence or absence of ammonia and the concentration thereof as in Application Example 7.

Application Example 9

A 20 mg amount of 6-butylamino-2,3-dihydro-5,8-dihydroxynaphthalene-1,4-dione was dissolved in 20 g of water containing 0%, 0.7%, 1.0%, 1.5%, or 2.0% of ammonia. Thus, five different dyeing solutions were prepared.

A 1.0 g amount of non-treated hair sample which contained a mixture of white and normal-color hair available from Staffs Co. (Japan) was immersed in each dyeing bath. The hair was dyed at a temperature of 30° C. for 45 minutes while agitating. Thereafter, the dyed hair was washed in 200 ml of water at a temperature of 30° C. for 5 minutes. The dyed hair sample contained no white hair after treatment in each case.

The resultant colors of the dyed hair samples were as follows:

| Ammonia (%) | Color |
|---|---|
| 0 | Orange |
| 0.7 | " |
| 1.0 | " |
| 1.5 | Bluish orange |
| 2.0 | " |

When the dyed hair samples were washed with a commercially available hair shampoo, followed by treating a commercially available hair rinse, no substantial color-bleeding remained substantially the same as before washing.

Application Example 10

A 20 mg amount of the naphthalene derivative used in Application Example 9 was dissolved in a mixed solvent of 10 g of water and 10 g of propylene glycol containing 0%, 0.7%, 1.0%, 1.5%, or 2.0% of ammonia. Thus, five different dyeing solutions were prepared.

The dyeing tests were carried out by using the dyeing solutions obtained above in the same manner as in Application Example 9. The dyed hair sample contained no white hair after treatment in each case and was dyed with bright color which was substantially the same as in Application Example 9.

Application Example 11

A 20 mg amount of the naphthalene derivative used in Application Example 9 was dissolved in a mixture of 20 g of water and 10 mg of an anionic surfactant (i.e., sodium alkylbenzene sulfonate) containing 0%, 0.7%, 1.0%, 1.5%, or 2.0% of ammonia. Thus, five different dyeing solutions were prepared.

The dyeing tests were carried out by using the dyeing solutions obtained above in the same manner as in Application Example 9. The dyed hair sample contained no white hair after treatment in each case and was dyed with bright color which was substantially the same as in Application Example 9.

Application Example 12

A 20 mg amount of the naphthalene derivative used in Application Example 9 was dissolved in a mixture of 10 g of water, 10 g of propylene glycol, and 10 mg of an anionic surfactant used in Application Example 11 containing 0%, 0.7%, 1.0%, 1.5%, or 2.0% of ammonia. Thus, five different dyeing solutions were prepared.

The dyeing tests were carried out by using the dyeing solutions obtained above in the same manner as in Application Example 9. The dyed hair sample contained no white hair after treatment in each case and was dyed with bright color which was substantially the same as in Application Example 9.

Application Example 13

A 20 mg amount of the naphthalene derivative used in Application Example 9 was dissolved in a mixture of 10 g of water and 10 g of ethanol containing 0%, 0.7%, 1.0%, 1.5%, or 2.0% of ammonia. Thus, five different dyeing solutions were prepared.

The dyeing tests were carried out by using the dyeing solutions obtained above in the same manner as in Application Example 9. The dyed hair sample contained no white hair after treatment in each case and was dyed with pretty color which was slightly pale color when compared to that in Application Example 9.

Application Example 14

A 20 mg amount of the naphthalene derivative used in Application Example 9 was dissolved in a mixture of 10 g of water, 2 g of ethanol, 8 g of propylene glycol, and 10 mg of an anionic surfactant used in Application Example 11 containing 0%, 0.7%, 1.0%, 1.5%, or 2.0% of ammonia. Thus, five different dyeing solutions were prepared.

The dyeing tests were carried out by using the dyeing solutions obtained above in the same manner as in Application Example 9. The dyed hair sample contained no white hair after treatment in each case and was dyed with bright color which was substantially the same as in Application Example 9.

Application Example 15

The dyeing tests of Application Example 14 were repeated in the same manner as in Application Example 14, except that the hair samples were bleach treated with a 5% aqueous hydrogen peroxide, before dyeing, at a temperature of 30° C. for 45 minutes.

As a result, the hair samples were also dyed with bright color as in Application Example 14.

The hair samples were dyed with stable color as in Application Examples 9 to 15 when the following naphthalene derivatives were used.

6-Amino-2,3-dihydro-5,8-dihydroxynaphthalene-1,4-dione, 6-methylamino-2,3-dihydro-5,8-dihydroxynaphthalene-1,4-dione, 6-ethylamino-2,3-dihydro-5,8-dihydroxynaphthalene-1,4-dione, and 6-propylamino-2,3-dihydro-5,8-dihydroxynaphthalene-1,4-dione.

Application Example 16

The dyeing tests were carried out in the same manner as in Application Example 9, except that 6-alkylamino-2,3-dihydro-5,8-dihydroxynaphthalene-1,4-diones prepared in Synthetic Examples 2 to 5 were used in lieu of the 6-butylamino-2,3-dihydro-5,8-dihydroxynaphthalene-1,4-dione used in Application Example 9.

The resultant colors of the dyed hair samples were as follows:

| Ammonia (%) | Color |
|---|---|
| 0 | Orange |
| 0.7 | " |
| 1.0 | " |
| 1.5 | Bluish orange |

| -continued | |
|---|---|
| Ammonia (%) | Color |
| 2.0 | " |

When the dyed hair samples were washed with a commercially available hair shampoo, followed by treating a commercially available hair rinse, no substantial color-bleeding remained substantially the same as before washing.

Application Example 17

A 20 mg amount of the naphthalene derivative used in Application Example 16 was dissolved in a mixed solvent of 10 g of water and 10 g of propylene glycol containing 0%, 0.7%, 1.0%, 1.5% or 2.0% of ammonia. Thus, five different dyeing solutions were prepared.

The dyeing tests were carried out by using the dyeing solutions obtained above in the same manner as in Application Example 16. The dyed hair sample contained no white hair after treatment in each case and was dyed with bright color which was substantially the same as in Application Example 16.

Application Example 18

A 20 mg amount of the naphthalene derivative used in Application Example 16 was dissolved in a mixture of 20 g of water and 10 mg of an anionic surfactant used in Application Example 11 containing 0%, 0.7%, 1.0%, 1.5% or 2.0% of ammonia. Thus, five different dyeing solutions in each case were prepared.

The dyeing test were carried out by using the dyeing solutions obtained above in the same manner as in Application Example 16. The dyed hair sample contained no white hair after treatment in each case and was dyed with bright color which was substantially the same as in Application Example 16.

Application Example 19

A 20 mg amount of the naphthalene derivative used in Application Example 16 was dissolved in a mixture of 10 g of water, 10 g of propylene glycol, and 10 mg of an anionic surfactant used in Application Example 11 containing 0%, 0.7%, 1.0%, 1.5%, or 2.0% of ammonia. Thus, five different dyeing solutions in each case were prepared.

The dyeing tests were carried out by using the dyeing solutions obtained above in the same manner as in Application Example 16. The dyed hair sample contained no white hair after treatment in each case and was dyed with bright color which was substantially the same as in Application Example 16.

Application Example 20

A 20 mg amount of the naphthalene derivative used in Application Example 16 was dissolved in a mixture of 10 g of water and 10 g of ethanol containing 0%, 0.7%, 1.0%, 1.5%, or 2.0% of ammonia. Thus, five different dyeing solutions in each case were prepared.

The dyeing tests were carried out by using the dyeing solution obtained above in the same manner as in Application Example 16. The dyed hair sample contained no white hair after treatment in each case and was dyed with pretty color which was slightly pale color when compared to that in Application Example 16.

Application Example 21

A 20 mg amount of the naphthalene derivative used in Application Example 16 was dissolved in a mixture of 10 g of water, 2 g of ethanol, 8 g of propylene glycol, and 10 mg of an anionic surfactant used in Application Example 11 containing 0%, 0.7%, 1.0%, 1.5%, or 2.0% of ammonia. Thus, five different dyeing solutions in each case were prepared.

The dyeing tests were carried out by using the dyeing solutions obtained above in the same manner as in Application Example 16. The dyed hair sample contained no white hair after treatment in each case and was dyed with bright color which was substantially the same as in Application Example 16.

Application Example 22

The dyeing test of Application Example 21 were repeated in the same manner as in Application Example 21, except that the hair samples were bleach treated with a 5% aqueous hydrogen peroxide, before dyeing, at a temperature of 30° C. for 45 minutes.

As a result, the hair samples were also dyed with bright color as in Application Example 21.

Application Example 23

The dyeing tests were carried out in the same manner as in Application Example 9, except that 6-benzylamino-2,3-dihydro-5,8-dihydroxynaphthalene-1,4-dione prepared in Synthetic Example 6 were used in lieu of the 6-butylamino-2,3-dihydro-5,8-dihydroxynaphthalene-1,4-dione used in Application Example 9.

As a result, the dyed hair sample contained no white hair after treatment. The resultant colors of the dyed hair were reddish brown to brown, which became bluish with the increase in the ammonia concentration in the dyeing solution.

When the dyed hair samples were washed with a commercially available hair shampoo, followed by treating a commercially available hair rinse, no substantial color-bleeding remained substantially the same as before washing.

Application Example 24

A 20 mg amount of the naphthalene derivative used in Application Example 23 was dissolved in a mixed solvent of 10 g of water and 10 g of propylene glycol containing 0%, 0.7%, 1.0%, 1.5% or 2.0% of ammonia. Thus, five different dyeing solutions were prepared.

The dyeing tests were carried out by using the dyeing solutions obtained above in the same manner as in Application Example 23. The dyed hair sample contained no white hair after treatment in each case and was dyed with bright color which was substantially the same as in Application Example 23.

Application Example 25

A 20 mg amount of the naphthalene derivative used in Application Example 23 was dissolved in a mixture of 20 g of water and 10 mg of an anionic surfactant (i.e., sodium alkylbenzene sulfonate) containing 0%, 0.7%, 1.0%, 1.5% or 2.0% of ammonia. Thus, five different dyeing solutions were prepared.

The dyeing tests were carried out by using the dyeing solutions obtained above in the same manner as in Application Example 23. The dyed hair sample contained no white hair after treatment in each case and was dyed with bright color which was substantially the same as in Application Example 23.

Application Example 26

A 20 mg amount of the naphthalene derivative used in Application Example 23 was dissolved in a mixture of 10 g of water, 10 g of propylene glycol, and 10 mg of an anionic surfactant used in Application Example 11 containing 0%, 0.7%, 1.0%, 1.5% or 2.0% of ammonia. Thus, five different dyeing solutions were prepared.

The dyeing tests were carried out by using the dyeing solutions obtained above in the same manner as in Application Example 23. The dyed hair sample contained no white hair after treatment in each case and was dyed with bright color which was substantially the same as in Application Example 23.

Application Example 27

A 20 mg amount of the naphthalene derivative used in Application Example 23 was dissolved in a mixture of 10 g of water and 10 g of ethanol containing 0%, 0.7%, 1.0%, 1.5% or 2.0% of ammonia. Thus, five different dyeing solutions were prepared.

The dyeing tests were carried out by the using the dyeing solutions obtained above in the same manner as in Application Example 23. The dyed hair sample contained no white hair after treatment in each case and was dyed with pretty color which was slightly pale color when compared to that in Application Example 23.

Application Example 28

A 20 mg amount of the naphthalene derivative used in Application Example 23 was dissolved in a mixture of 10 g of water, 2 g of ethanol, 8 g of propylene glycol, and 10 mg of an anionic surfactant used in Application Example 11 containing 0%, 0.7%, 1.0%, 1.5% or 2.0% of ammonia. Thus, five different dyeing solutions were prepared.

The dyeing tests were carried out by using the dyeing solution obtained above in the same manner as in Application Example 23. The dyed hair sample contained no white hair after treatment in each case and was dyed with bright color which was substantially the same as in Application Example 23.

Application Example 29

The dyeing test of Application Example 28 were repeated in the same manner as in Application Example 28, except that the hair samples were bleach treated with a 5% aqueous hydrogen peroxide, before dyeing, at a temperature of 30° C. for 45 minutes.

As a result, the hair samples were also dyed with bright color as in Application Example 28.

Application Example 30

The dyeing tests were carried out in the same manner as in Application Example 9, except that 6-hydroxyethylamino-2,3-dihydro-5,8-dihydroxynaphthalene-1,4-dione prepared in Synthetic Example 7 were used in lieu of the 6-butylamino-2,3-dihydro-5,8-dihydroxynaphthalene-1,4-dione used in Application Example 9.

As a result, the dyed hair sample contained no white hair after treatment. The resultant colors of the dyed hair were reddish brown to brown, which became bluish with the increase in the ammonia concentration in the dyeing solution.

When the dyed hair samples were washed with a commercially available hair shampoo, followed by treating a commercially available hair rinse, no substantial color-bleeding remained substantially the same as before washing.

Application Example 31

A 20 mg amount of naphthalene derivative used in Application Example 30 was dissolved in a mixed solvent of 10 g of water and 10 g of propylene glycol containing 0%, 0.7%, 1.0%, 1.5% or 2.0% of ammonia. Thus, five different dyeing solutions were prepared.

The dyeing tests were carried out by using the dyeing solutions obtained above in the same manner as in Application Example 30. The dyed hair sample contained no white hair after treatment in each case and was dyed with bright color which was substantially the same as in Application Example 30.

Application Example 32

A 20 mg amount of 6-methoxyethylamino-2,3-dihydro-5,8-dihydroxynaphthalene-1,4-dione prepared in Synthetic Example 8 was dissolved in a mixture of 20 g of water and 10 mg of an anionic surfactant used in Application Example 11 containing 0%, 0.7%, 1.0%, 1.5% or 2.0% of ammonia. Thus, five different dyeing solutions were prepared.

The dyeing tests were carried out by using the dyeing solutions obtained above in the same manner as in Application Example 30. The dyed hair sample contained no white hair after treatment in each case and was dyed with bright color which was substantially the same as in Application Example 30.

Application Example 33

A 20 mg amount of the naphthalene derivative used in Application Example 32 was dissolved in a mixture of 10 g of water, 10 g of propylene glycol, and 10 mg of an anionic surfactant used in Application Example 11 containing 0%, 0.7%, 1.0%, 1.5% or 2.0% of ammonia. Thus, five different dyeing solutions were prepared.

The dyeing tests were carried out by using the dyeing solutions obtained above in the same manner as in Application Example 32. The dyed hair sample contained no white hair after treatment in each case and was dyed with bright color which was substantially the same as in Application Example 32.

Application Example 34

A 20 mg amount of the naphthalene derivative used in Application Example 30 was dissolved in a mixture of 10 g of water and 10 g of ethanol containing 0%, 0.7%, 1.0%, 1.5% or 2.0% of ammonia. Thus, five different dyeing solutions were prepared.

The dyeing tests were carried out by using the dyeing solutions obtained above in the same manner as in Application Example 30. The dyed hair sample contained no white hair after treatment in each case and was dyed with pretty color which was slightly pale color when compared to that in Application Example 30.

Application Example 35

A 20 mg amount of the naphthalene derivative used in Application Example 30 was dissolved in a mixture of 10 g of water, 2 g of ethanol, 8 g of propylene glycol, and 10 mg of an anionic surfactant used in Application Example 11 containing 0%, 0.7%, 1.0%, 1.5% or 2.0% of ammonia. Thus, five different dyeing solutions were prepared.

The dyeing tests were carried out by using the dyeing solutions obtained above in the same manner as in Application Example 30. The dyed hair sample contained no white hair after treatment in each case and was dyed with bright color which was substantially the same as in Application Example 30.

Application Example 36

The dyeing tests of Application Example 35 were repeated in the same manner as in Application Example 35, except that the hair samples were bleach treated with a 5% aqueous hydrogen peroxide, before dyeing, at a temperature of 30° C. for 45 minutes.

As a result, the hair samples were also dyed with bright color as in Application Example 35.

We claim:

1. A naphthalene derivative having the general formula:

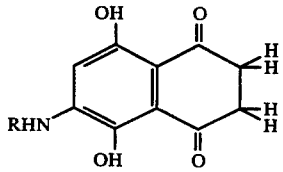

wherein R represents hydrogen, an alkyl group having 1 to 8 carbon atoms, an $R^1O(CH_2)_n$ group, or a benzyl group, $R^1$ represents hydrogen or a lower alkyl group, and n represents an integer of 2 or 3.

2. A naphthalene derivative as claimed in claim 1, wherein R is hydrogen.

3. A naphthalene derivative as claimed in claim 1, wherein R is an alkyl group having 3 to 8 carbon atoms.

4. A naphthalene derivative as claimed in claim 1, wherein R is a benzyl group.

5. A naphthalene derivative as claimed in claim 1, wherein R is $-CH_2CH_2OH$ or $-CH_2CH_2OCH_3$.

6. A hair dye composition comprising a naphthalene derivative having the general formula:

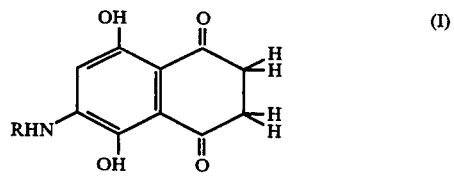

wherein R represents hydrogen, an alkyl group having 1 to 8 carbon atoms, an $R^1O(CH_2)_n$ group, or a benzyl group, $R^1$ represents hydrogen or a lower alkyl group, and n represents an integer of 2 or 3.

7. A hair dye composition as claimed in claim 6, wherein the concentration of the naphthalene derivative is 0.01% by weight or more.

8. A hair dye composition as claimed in claim 6, wherein the concentration of the naphthalene derivative is 0.05% to 5% by weight.

9. A hair dye composition as claimed in claim 6 comprising 0.01% to 5.0% by weight of the naphthalene derivative having the general formula (I), 10% to 20% by weight of a surfactant, 10% to 15% by weight of an alcohol, 10% to 15% by weight of a humectant, and a balance of water.

* * * * *